United States Patent [19]
Rose

[11] Patent Number: 5,816,259
[45] Date of Patent: Oct. 6, 1998

[54] METHOD FOR THE DIAGNOSIS AND TREATMENT OF CANCER BY THE ACCUMULATION OF RADIOACTIVE PRECIPITATES IN TARGETED CELLS

[76] Inventor: Samuel Rose, 5562 Marshall St., Oakland, Calif. 94608

[21] Appl. No.: 782,380

[22] Filed: Jan. 13, 1997

[51] Int. Cl.⁶ .................................................. A61B 19/00
[52] U.S. Cl. ...................................... 128/898; 424/178.1
[58] Field of Search ..................... 424/94.1, 1.11–1.89, 424/178.1–183.1; 435/7.1–7.24; 544/313; 128/898

[56] References Cited

U.S. PATENT DOCUMENTS

| | | | |
|---|---|---|---|
| 4,466,951 | 8/1984 | Pittman . | |
| 4,957,735 | 9/1990 | Huang | 424/85.8 |
| 5,082,930 | 1/1992 | Nicolotti et al. | 530/402 |
| 5,443,953 | 8/1995 | Hansen et al. | 424/1.49 |
| 5,501,854 | 3/1996 | Raso | 424/136.1 |

*Primary Examiner*—Mickey Yu
*Assistant Examiner*—Kelly O'Hara
*Attorney, Agent, or Firm*—John Q. McQuillan

[57] ABSTRACT

A method for the accumulation of trace-labeled or therapeutic insoluble molecules in targeted cells of a living host for purposes including diagnosis, therapy, and research in cell biology. The method enables soluble precipitable materials, which can be trace-labeled or therapeutic, to be made to accumulate as non-digestible precipitates in targeted cells as a result of enzyme action within the targeted cells. Accumulation is achieved by administering to the living host a soluble binary reagent having a targeting agent attached to a chemical agent which is a soluble precipitable material. The binary reagent binds to antigenic receptors on targeted cells which endocytosed the binary reagent and transport it into the lysosomes where enzymes detach the soluble precipitable material from the targeting agent, causing it to precipitate, accumulate, and be retained in the cells. Continuing the administration of the binary reagent forms an accumulation of precipitate which becomes a stable insoluble tracer agent or a stable insoluble therapeutic agent in the targeted cells. The method can be applied to the diagnosis and scanning of certain diseased states, and to the therapy of certain diseased states, such as cancer, by generating supra-lethal micro-regions of radiation around targeted cells called Hot-Spots which are capable of killing, non-specifically, all cells in the immediate micro-region.

36 Claims, 9 Drawing Sheets

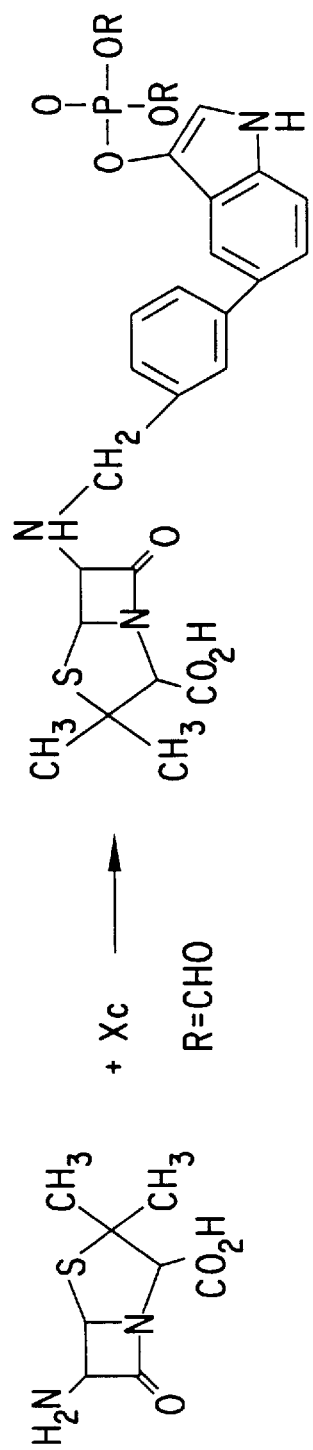
FIG. 13
FIG. 11
FIG. 10

METHOD FOR THE DIAGNOSIS AND TREATMENT OF CANCER BY THE ACCUMULATION OF RADIOACTIVE PRECIPITATES IN TARGETED CELLS

The present invention has developed a method for forming and accumulating in targeted cells an insoluble trace-labeled precipitate for at least one of the following procedures including therapy, diagnosis, and monitoring of the living host. The insoluble trace-labeled precipitate being composed of materials which prevent the insoluble trace-labeled precipitate from diffusing out of targeted cells.

BACKGROUND

1. Field of the Invention

A considerable portion of world-wide research efforts in the diagnostic scanning and therapy of cancer and other disease states use targeting agents which carry soluble trace-labeled and soluble therapeutic agents to the targeted cells. These targeting agent complexes fail to diagnose and treat cancer successfully because they are unable to circumvent three universally present obstacles: (1) the agents do not target, label, or kill all the cancer cells because they do not exhibit specificity for all the cancer cells, (2) the agents also target, label, or kill normal cells because they do not exhibit specificity exclusively for cancer cells, and (3) the agents are not potent enough to kill resistant cancer cells or to overcome the ability of cancer cells to adapt and become resistant to the cell killing agents.

Current approaches also fail because the tracer or therapeutic agent is a soluble metabolizable material. The tracer or therapeutic agent is not delivered in sufficient amounts and the agent itself does not remain in the targeted cells for an extended period of time. Because it is a soluble metabolizable material, it leaves the targeted cells, diffuses throughout the body, and enters and non targeted cells where it exhibits its tracer or therapeutic action.

These obstacles have been overcome in special cases by the local administration of an insoluble material. Insoluble agents are highly effective for the diagnosis or treatment of certain disease states, where the diseased state is localized and confined to a tissue of the body, and where that tissue is accessible to local injection. In such cases, the local injection of an insoluble agent results in intense local action of the agent and in minimal systemic effect. However, the injection of insoluble materials as a therapeutic procedure is limited to tissues which are accessible to local injection and to cases where the diseased state is localized and confined so that the local injection can have a profound effect on the local tissue and where it is not necessary to treat tissues outside of the local area. Unfortunately, with regard to the treatment of cancer, in most cases the use of insoluble agents has not been a successful therapeutic alternative.

The present invention is directed to obtaining the advantages of both the soluble and insoluble agents by the administration of a targeted soluble material which becomes insoluble and precipitates when it reaches the targeted area. In this way, the present invention obtains the targeting advantages of soluble drugs and the localized intensity of insoluble reagents.

2. Prior Art

In many normal and disease states, it is desirable to target therapeutic and/or tracer chemicals to specific cell types. Two problems exist in such targeting. The first problem is how to cause the targeting to be specific for certain cell types. The second problem is how to accumulate and retain the therapeutic and/or tracer chemical in the region of the targeted cells for as long as possible in order to maximize the effect on the targeted cells, and at the same time minimize the effect on non-targeted cells by preventing the therapeutic and/or tracer chemical from leaving the region of the targeted cells, diffusing away, and reaching the regions of non-targeted cells.

Progress has been made on the first problem by accumulating the therapeutic and/or tracer agent inside targeted cells. This has been achieved by constructing a binary reagent by covalently attaching the therapeutic or tracer chemical to proteins, such as antibodies, hormones, or peptides which act as targeting agents (Ghose T. and Blair A. H. 1987, CRC Critical Reviews of Therapeutic Drug Carrier Systems, 3,262–359; Blakely et al. 1988, Progress in Allergy, 45,50–9). The protein targeting agent moiety of the binary reagent binds to endocytosing antigenic receptors on certain cell types, called target cells, and delivers the therapeutic or tracer chemical agent to the desired target cells. The binding of the targeting agent to the antigenic receptor on the target cells induces the target cells to undergo receptor mediated endocytosis which causes the cells to "swallow" the receptor and bound binary reagent, and to transport the receptor and binary reagent to lysosome vacuoles. The lysosome vacuoles have an acidic environment and contain a high concentration of numerous proteolytic, glycanolytic, nuclease, and lipolytic enzymes. Once inside the lysosomes, the receptors are released from the binary reagents and recycle back to the cell surface to bind more binary reagents and to thus continue repeating the receptor mediated endocytosis process. In this manner, each receptor can recycle 5 to 10 times per hour. Inside the lysosomes, the targeting agent moiety of the binary reagent is digested, and the therapeutic or tracer chemical is released as a free, soluble molecule. In this free state the chemical exerts its tracer or pharmacological therapeutic action.

Cytotoxic drugs, toxins, dyes, antidotes to toxic drugs, and molecules carrying radioisotopes have been delivered to cells by this means (Ali et al. 1990, Cancer R. Suppl.. 50,783–788; Wu et al. 1985, Hepatology 1985, 5, 709–713; Wu et al. 1983, Proc. Nat. Acad. Sci., 80, 3078–3080; Firestone Raymond 1994, Bioconjugate, 5, 105–113; C. Rushfeldt and Brad Smedsrod 1993, Cancer Research 1993, 53, 658–662; Pittman et al. 1983, Biochem. J. 212, 791–800; Jansen et al. 1992, Hepatology 18, 146–152; Daniel A. Vallera 1994, Blood, 83, 309–317; A. Mukhopadhyay and S. K. Basu 1990, Biotechnology and Applied Biochem. 12, 529–536).

Some progress has also been made regarding the second problem of the attached therapeutic and/or tracer chemical leaving the targeted cells. The second problem has been partly solved by trapping the released chemical in the lysosomes of the targeted cell. For example, one approach to the problem of intra-cellular trapping that has been described uses a common disaccharide, sucrose, as a marker of fluid endocytosis. Since mammalian cells lack the necessary glycosidase, the sucrose is not digested, and since sucrose is unable to rapidly cross the cell membrane, the sucrose is partially trapped in the cell. Thus, the amount of sucrose which is trapped can be used as an approximate measure of sucrose uptake.

Taking advantage of these properties of sucrose, a technique was developed for determining the sites of degradation of plasma proteins, by using the proteins as targeting agents which are covalently attached to radio-sucrose to make a binary reagent. The binary reagent is introduced into targeted cells by receptor mediated endocytosis to measure the rate of degradation of the targeting agent protein. After the administration and receptor mediated endocytosis of the binary reagent, the protein targeting agent moiety of the binary reagent is enzymatically digested, causing the release of the soluble radio-sucrose molecules as a free molecules. Since sucrose is not degraded and remains partially trapped within the cell, the amount which has accumulated in the cell can be used as an approximate measure of the amount degradation of the protein targeting agent by the targeted cells (Pittman and Steinberg 1978, Biochem. Biophys. Res. Commun. 81, 1254–1259; Pittman et al. 1979, J. Bio. Chem.; 254, 6876–6879; Pittman et al. 1979, Proc. Natl. Acad. Sci. USA 76,5345–5349).

More recently, it has been shown that soluble cellobiose can be used in a similar manner to sucrose. Cellobiose can be linked by a non-metabolizable bond to the therapeutic or tracer chemical, so that the soluble cellobiose and the attached therapeutic or tracer chemical, once free from its attachment to the targeting agent, accumulates in the targeted cells (Pittman et al. 1983, Biochem. J. 212,791–800; Pittman, 1984, U.S. Pat. No. 4,466,951). The cellobiose method has certain advantages over the use of sucrose.

Nevertheless, both the soluble sucrose and cellobiose have the disadvantage in that the accumulated carbohydrate, with or without an attached therapeutic chemical, slowly leaves the cell. Therefore, cells cannot continue to accumulate increasing amounts of carbohydrate. There is the added disadvantage that the accumulated carbohydrate can diffuse away from the targeted cell and reach cells which were not targeted.

SUMMARY OF THE PRESENT INVENTION

It is an object of the present invention to provide a method for accumulating trace-labeled or therapeutic soluble precipitable materials as non-digestible tracelabeled or therapeutic precipitates in targeted cells as a result of enzyme action within the targeted cells. The accumulation of the precipitate is achieved by the administration of a soluble binary reagent made by attaching a targeting agent to a tracelabeled or therapeutic soluble precipitable material. The binary reagent binds to antigenic receptors on the targeted cells, which causes the cell to endocytose the binary reagent and transport it to the lysosomes in the cell. The enzymes and/or the acid environment inside the lysosomes detach the trace-labeled or therapeutic soluble precipitable material from the targeting agent and enable the soluble precipitable material to precipitate, accumulate, and be retained for an extended period in the cell. The amount of precipitate which can be made to accumulate increases with the continued administration of the binary reagent.

It is a further object of the present invention to use the accumulation of precipitate for at least one of the following procedures including diagnosis, therapy, biological research, and monitoring.

BRIEF DESCRIPTION OF THE DRAWINGS

FIG. 10 shows molecule Xc, indoxylphosphate dibenzylester.

FIG. 11 shows the attachment of penicillin to the benzene ring.

FIG. 13 shows cephalosporin.

DESCRIPTION OF THE PREFERRED EMBODIMENTS

The present invention is a method for accumulating an insoluble trace-labeled precipitate in targeted cells of a living host for at least one of the following procedures including diagnosis, therapy, biological research, and monitoring.

Figure 1:
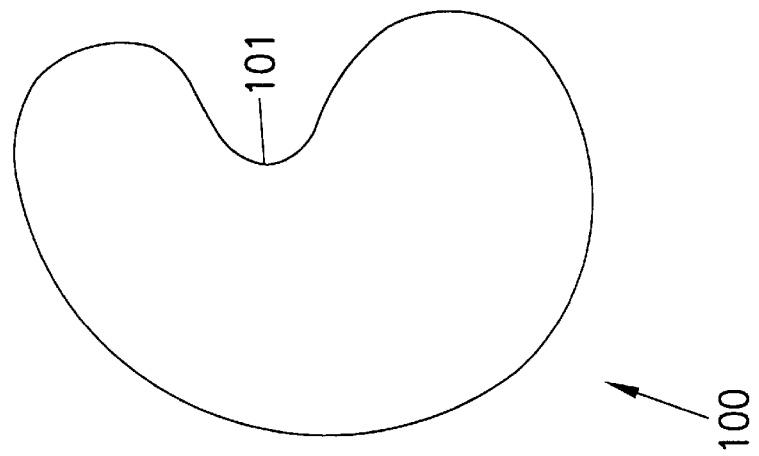
FIG. 1 shows the first target cells.

The living host being composed of at least two populations of cells, the cells endogenously making and containing products including at least sulphated glycosaminoglycans and natural intracellular enzymes in the lysosomes. As shown in FIG. 1 the first population of cells being the first target cells 100, the first target cells 100 having a first antigenic receptor 101 which is capable of binding a first targeting agent, the first antigenic receptor being capable of endocytosis when the first targeting agent binds to the first antigenic receptor. The second population of cells being nontarget cells which are the remainder of the cells.

Figure 2:
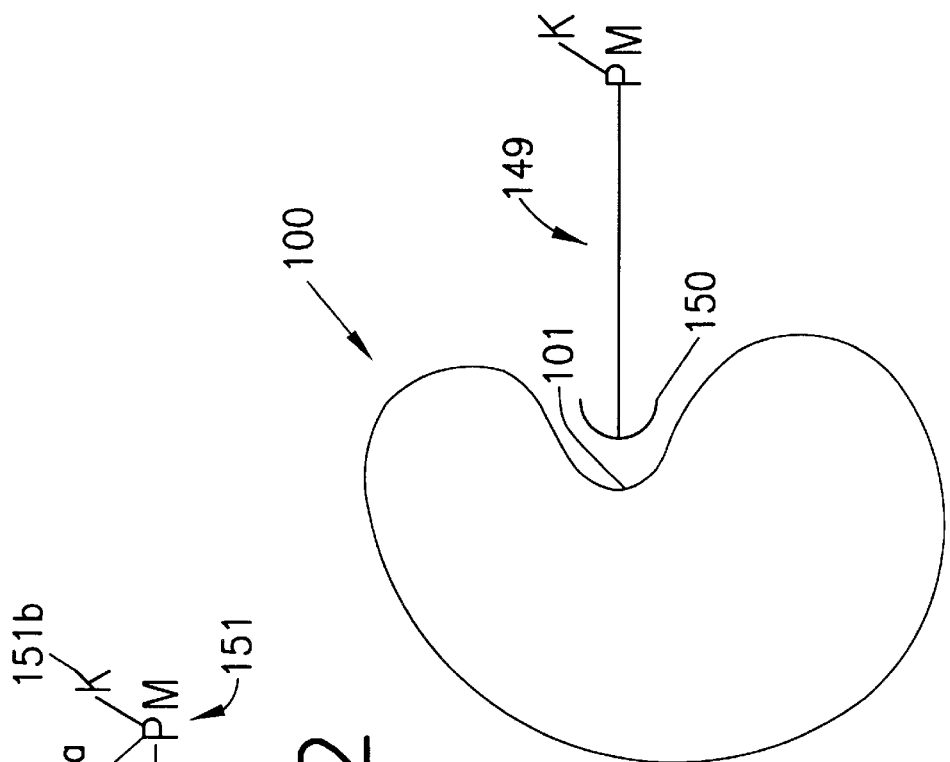
FIG. 2 shows the binary reagent.

The method of the invention comprising the step of introducing into the living host a binary reagent. FIG. 2 shows the binary reagent 149 which is introduced to the living host, the binary reagent having two moieties, the first moiety being the first targeting agent 150 which has the substantial affinity for the first antigenic receptors, the second moiety of the binary reagent 149 being a soluble precipitable material 151 having a first antigenic epitope 151*a* and a second antigenic epitope 151*b* is attached to the first targeting agent 150.

Figure 3:
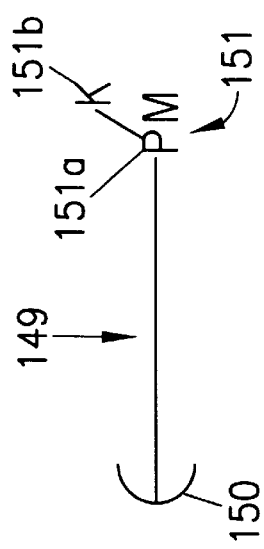
FIG. 3 shows the binary reagent binding to the first target cells.

As shown in FIG. 3 the first targeting agent 150 of the binary reagent 149 attaches to the first antigenic receptor 101 of the first target cancer cells 100, thereby permitting the binary reagent 149 to be endocytosed into the lysosomes of the first target cancer cells.

Figure 4:
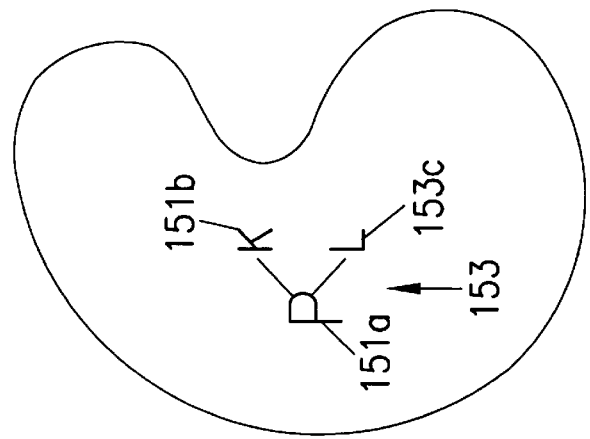
FIG. 4 shows the formation of precipitate in the first target cells.

The endocytosing and the natural intra-cellular enzymes in the lysosomes of the cells, as illustrated in FIG. 4, causes the soluble precipitable material 151 to detach from the first targeting agent and enables the detached soluble precipitable material to form a precipitate 153 which has an antigenic epitope. The antigenic epitope on the precipitate 153 being the same antigenic epitope as the soluble precipitable material and being the first antigenic epitope 151a The precipitate having the second antigenic epitope 151b, and further having a neo-antigenic third epitope 153c, the precipitate 153 accumulating in the lysosomes within the first target cancer cells 100.

Figure 5:
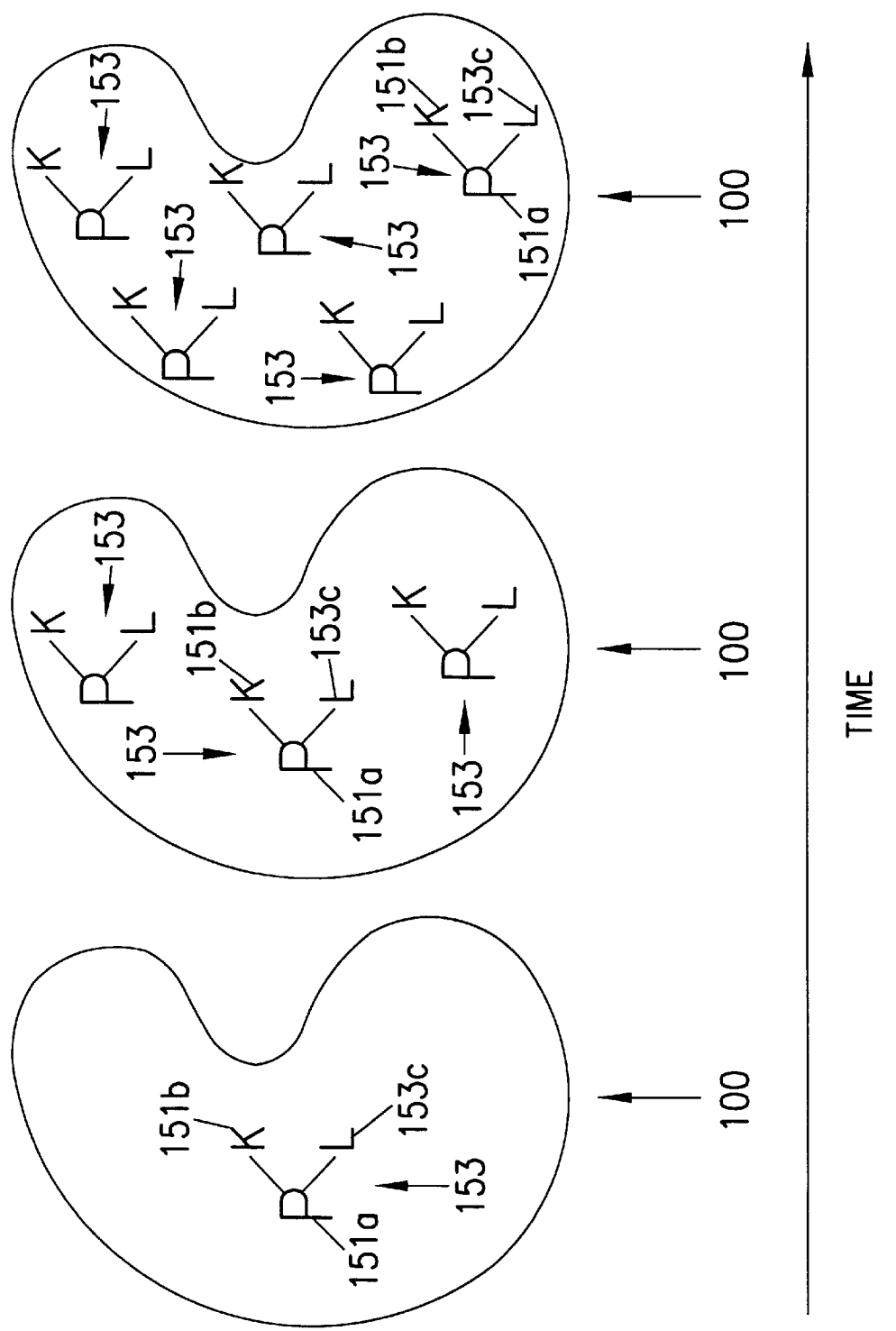
FIG. 5 shows the accumulation of precipitate forming in the first target cells.
Figure 14:
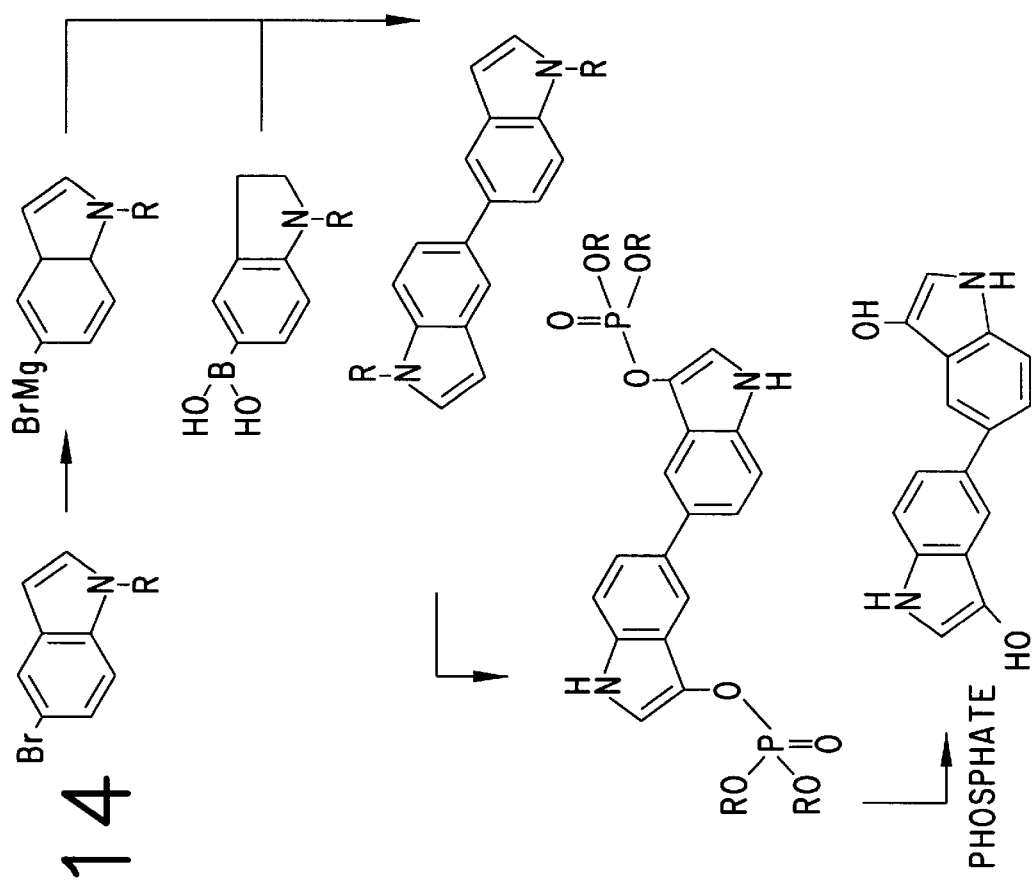
FIG. 14 shows the attachment of 2 indoxyl phosphate via the benzene ring, note that both ends have phosphate groups which can be cleaved.
Figure 12:
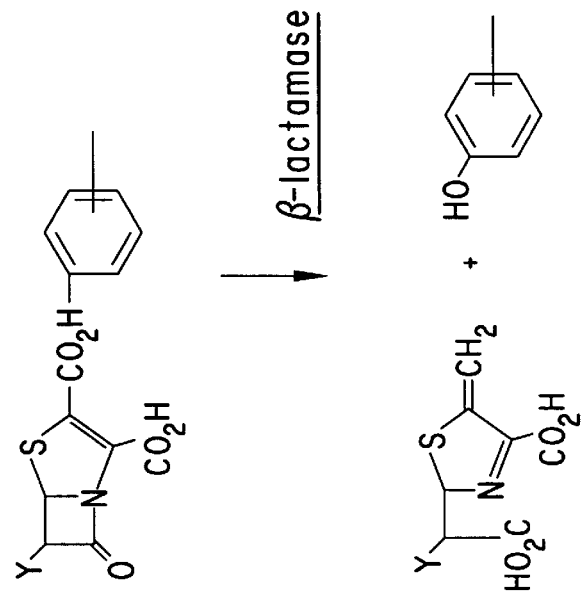
FIG. 12 shows the attachment of penicillin to the benzene ring where the bond between the benzene ring and the penicillin is unaffected by mammalian enzymes.
Figure 16:
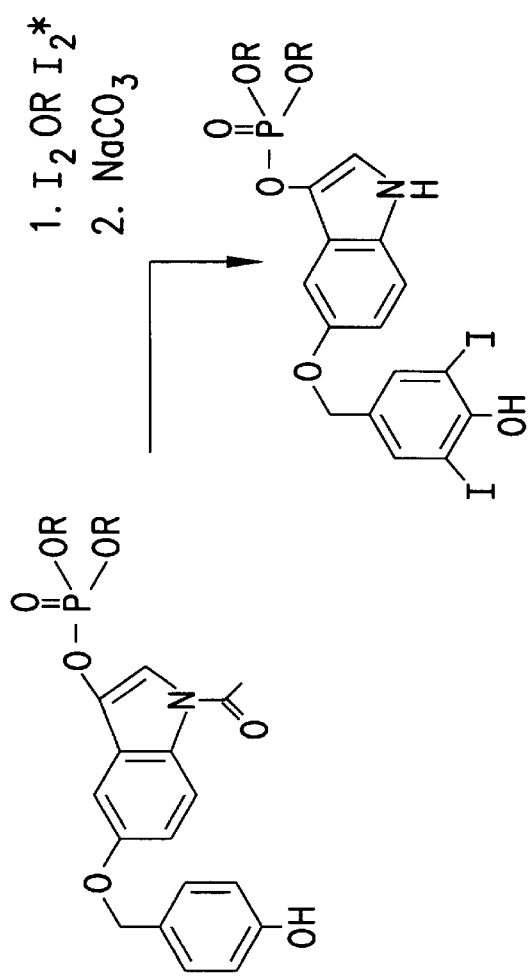
FIG. 16 shows the method of radio-iodinating indoxyl compounds to make iodinated (parahydroxy-benzyl ether of 5-hydroxy indoxyl phosphate).
Figure 15:
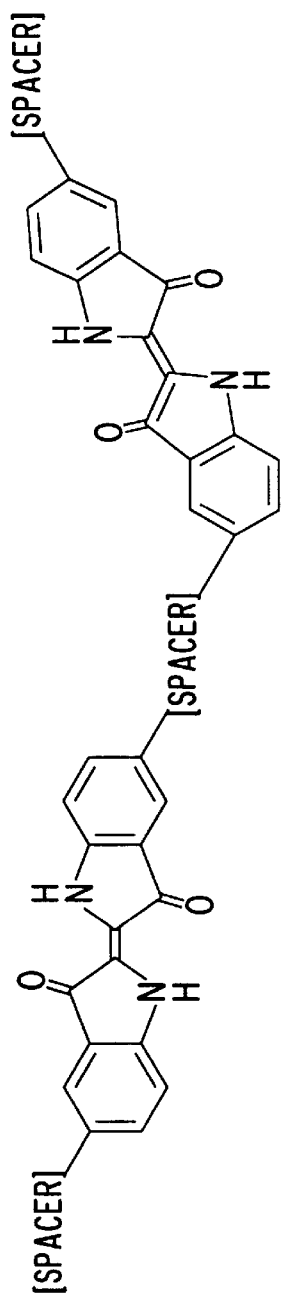
FIG. 15 shows a linear polymer formed by dimerization of 2 bi-indoxyl compounds attached at their benzene ring via a spacer.
Figure 17:
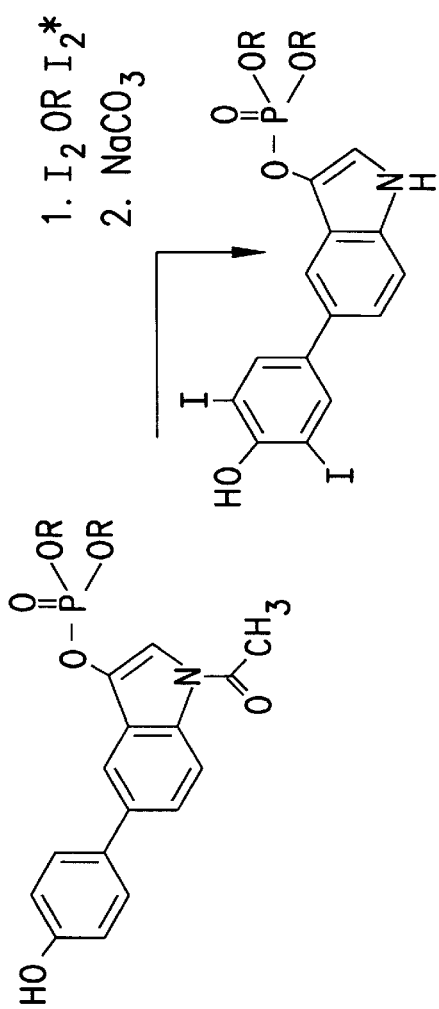
FIG. 17 shows the method of radio-iodinating indoxyl compounds to make iodinated (parahydroxy-phenyl) substituted at the 5 position.
Figure 18:
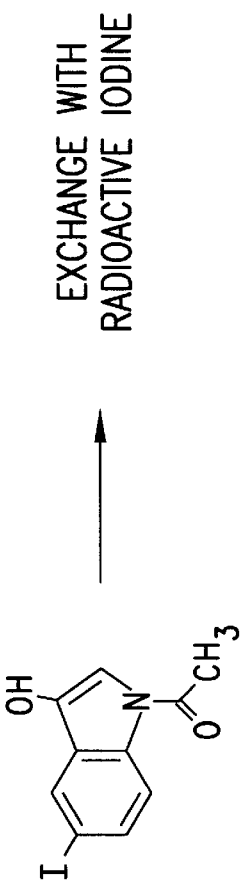
FIG. 18 shows the method of radio-iodinating indoxyl compounds where 1-acetyl-5 iodo-3-hydroxyindole is exchanged with radioactive iodine.

The method of the present invention further comprises the step of continuing the introducing of the binary reagent into the living host to increase the amount of the accumulation of the precipitate. FIG. 5 shows the accumulation of the precipitate 153 in the first target cancer cells 100 to form a plurality of antigenic epitopes which is proportional to the amount of accumulation. Accumulation of the precipitate is achieved by continuing the introducing of the binary reagent 149 into the living host and allowing more soluble precipitable material 151 to precipitate within the cells, the continued formation of precipitate 153 causing an accumulation of precipitate in the first target cancer cell 100 to occur. The precipitate 153 having a first antigenic epitope 151a, a second antigenic epitope 151b, and a neo-antigenic third epitope 153c, and the accumulation of precipitate 153 thereby becoming a plurality of epitopes 151a, 151b, 153c.

The introducing of the binary reagent, the permitting of the cell to undergo endocytosis, and the continuing of the introducing of the binary reagent results in the formation of a precipitate inside the target cells and accumulation of the precipitate inside the first target cells.

The accumulation step is achieved by exploiting receptor mediated endocytosis, the natural on-going "swallowing" process of cells, the precipitate itself being stable and non-digestible by mammalian enzymes. Unlike soluble chemicals, the precipitate cannot leave the cells. For these reasons, the process of precipitate accumulation is a cumulative time dependent process. It is possible, by the continued administration of the binary reagent, to accumulate any desired amount of precipitate. For example, in 100 hours, 1000 times as many molecules of precipitate can be accumulated in the cell as there are receptors on the cell surface at any time.

Intra-cellular formation and accumulation of the precipitate relies on the action of endogenous lysosomal enzymes and/or the acidic pH in the lysosomes to form the precipitate by detaching the precipitable material from the targeting agent and converting the detached precipitable material into a precipitate. Precipitation does not occur in any appreciable amounts in the extra-cellular body fluid because this fluid does not contain active lysosomal enzymes. Any lysosomal enzyme which "accidentally" enters the extra-cellular fluid is largely inactivated by naturally circulating protein antagonists and by the neutral pH found in the extra-cellular fluid.

Two classes of precipitable materials can be delivered and made to accumulate in the form of a precipitate in the lysosomes of targeted cells. The first class of precipitable materials are inherently soluble in aqueous medium and can be readily attached to the protein or peptide targeting agent in aqueous medium by conventional means to make a soluble binary reagent. The attachment is a non-random controlled process and is effected by ionic and Van Der Waal forces, or by covalent bonding via functional groups in the peptide such as: SH, NH2, and CO2H and by substitution into the aromatic portion of tyrosine, tryptophan, and histidine. Structural analysis of the binary reagent is made by mass spectroscopy, and the affinity of the targeting agent moiety of the binary reagent is measured to determine if it has been altered during the chemical manipulations required for the attachment of the precipitable material to the targeting agent. Aqueous soluble precipitable materials require the lysosomal enzymes and/or the acidic environment in the lysosomes both to detach the soluble precipitable material from its attachment to the targeting agent and to convert the detached soluble precipitable material into a precipitate which then accumulates in the lysosomes of the targeted cells.

One example of the first class of soluble precipitable materials is made by converting chemical X to a soluble X-Y which is a soluble material compatible with a reaction medium for the protein or peptide targeting agent and can be attached in aqueous medium to the targeting agent to make a soluble binary reagent. The soluble binary reagent remains soluble because the attachment of the X-Y to the targeting agent does not disturb the linkage of X to Y. After the targeting agent of the soluble binary reagent binds to the targeted cell receptor, it activates the cell to undergo receptor mediated endocytosis which transports the soluble binary reagent to the lysosome of the cell. In the acidic, enzyme rich environment of the lysosome, the X-Y is cleaved from its attachment to the targeting agent by an esterase or peptidase and/or the acidic environment. The X-Y bond is cleaved by a lysosomal enzyme to create a highly reactive soluble intermediate molecule, Xa. The Xa molecule is readily and extremely rapidly oxidized to form a soluble oxidized molecule Xb which spontaneously and covalently self-condenses or dimerizes to create a new molecule which is insoluble and immediately precipitates. Because a new molecule is formed by the dimerization, the core structure of the precipitate has a neo-antigenic epitope which is not present on the X-Y, Xa, or Xb.

Figure 8:
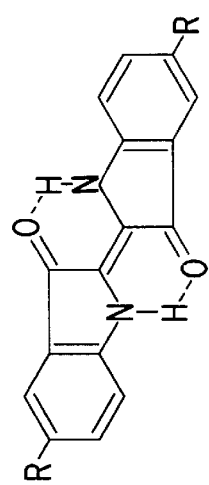
FIG. 8 shows the dimerization of two indoxyl molecules to form indigo.
Figure 9:
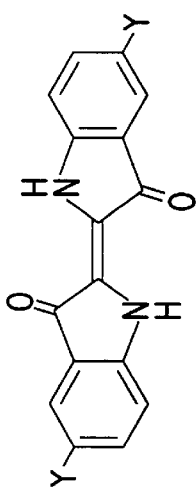
FIG. 9 shows the substituted indigos.
Figure 6:
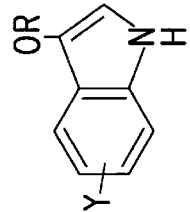
FIG. 6 shows the general structure of indole esters substituted in the benzene ring.
Figure 7:
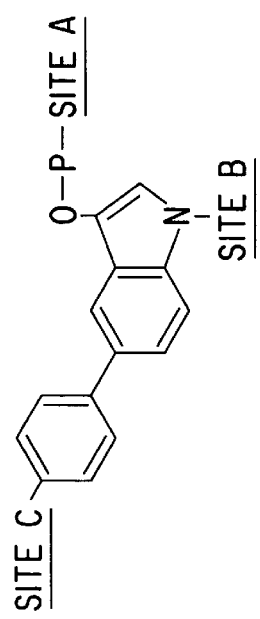
FIG. 7 shows the three sites of attachment of the targeting agent to indoxyl phosphate.

A specific example of this procedure is the application of an indoxyl, the general structure of indoxyl esters substituted in the benzene ring is shown in FIG. 6, where R can be one of many chemicals including phosphate, sulphate, or various carbohydrates and where Y can be aryl, halogen, and alkyl. Indoxylphosphate, as examples of X-Y, which is freely soluble, can be attached in an aqueous medium to the protein or peptide targeting agent in three ways: (1) by non-covalent Van Der Waal forces, (2) by non-covalent ionic forces, or (3) by covalent bonds at 3 sites. The three sites for covalent bonding on the indoxylphosphate are shown in FIG. 7. In each of these methods of attachment, the indoxylphosphate (X-Y) is cleaved from the targeting agent, and the phosphate of the indoxylphosphate is cleaved by lysosomal phosphatase enzymes to liberate indoxyl (Xa) which is a highly reactive intermediate indoxyl. The indoxyl (Xa) is readily and extremely rapidly oxidized to form (Xb), and once in the oxidized form the (Xb) spontaneously self-condenses or dimerizes, as shown in FIG. 8 to form a new molecule which is insoluble and precipitates spontaneously as an indigo dye as illustrated in FIG. 9 where Y can be aryl, halogen, hydoxyl, and alkyl. The insoluble indigo dye, being a molecule different from the indoxyl compounds and the indoxyl intermediates from which the indigo dye was formed, has an antigenic epitope not found on the indoxyl compounds or the indoxyl intermediates. This antigenic epitope is a neo-antigenic third epitope.

The oxidation and dimerization of indoxyl proceeds at a slower rate at pH 4.5 of the lysosome vacuoles in which the dimerization takes place compared to the rate at a neutral or alkaline pH. This slower rate could allow some of the soluble indoxyl molecules and their intermediates to exit the cell prior to dimerizing and precipitating inside the cell, the exited molecules being free to dimerize and precipitate in the extra-cellular fluid. Various modifications can be made to the indoxylphosphate so that the rate of soluble indoxyl molecules exiting the cell is greatly reduced, and more time would be available for the dimerization and precipitation to take place, thus reducing the amount of free indoxyl and the intermediates from exiting the cell.

A first chemical, for example cellobiose, can be attached to the benzene ring of the indoxylphosphate by reductive amination, involving an amino group on the benzene ring and the reducing end (aldehyde) of the cellobiose. The result is an alkyl amino group, similar to that formed when polylysine is lactosylated by reductive amination. The resultant bond is incapable of being cleaved by mammalian enzymes, and because the first chemical has been selected to be a chemical which remains partially trapped within cells, the first chemical reduces the rate of exit of the soluble indoxyl molecules. The attachment of the first chemical to the benzene ring of the indoxylphosphate will not interfere with the release of the indoxylphosphate from its protein attachment, or the ability of the lysosome enzyme to cleave the phosphate bond, or the ability of the indoxyl to be oxidized, to dimerize, and to precipitate.

Further modifications can be made to the indoxylphosphate so that the precipitate formed from the indoxylphosphate has certain desired characteristics. For example, a second chemical with an antigenic epitope, such as penicillin, can be covalently attached to the indoxyl (X-Y), so that the indigo precipitate will have a second antigenic epitope in addition to the neo-antigenic third epitopes which developed as a result of dimerization.

The penicillin-indoxyl compound can be prepared by a number of methods. In the first method, the 6-amino-penicillanic acid (6-APA) moiety is attached to a substituted indoxylphosphate dibenzylester, of the type Xc as shown in FIG. 10. Various modes of attachment of the 6-amino-penicillanic acid can be used, but the preferred mode is reductive amination which leads to a non-hydrolyzable covalent bond illustrated in FIG. 11 where R is CHO. Beta lactamase acts on the penicillin to open up the lactam ring which prevents antibodies and peptides having an affinity to bind to penicillin from binding to the precipitate. In the second method, as shown in FIG. 12, the penicillin is attached to the benzene ring in a way which is unaffected by mammalian enzymes, but is cleaved by beta-lactamase which prevents antibodies and peptides having an affinity to bind to penicillin from binding to the precipitate. Many other types of molecules, particularly any amino compound, can be attached to Xc, through the hydroxy, amino, and carboxyl groups. The attachment of the second chemical having a second antigenic epitope can be achieved without interfering with any of the steps required for final precipitation to occur. The attachment of the second chemical will not interfere with the release of the indoxylphosphate from its protein attachment, will not interfere with the ability of the phosphatase enzyme to cleave the phosphate bond, and will not interfere with the ability of the indoxyl to precipitate. Exactly the same reactions can be applied to cephalosporin as shown in FIG. 13. The second antigenic epitope on the indigo precipitate provides a number of substantial advantages which are described later.

As shown in FIG. 14, a further modification is made by covalently attaching two indoxylphosphate molecules together at a position on the benzene ring to make a bi-indoxylphosphate. Note that both ends have phosphate groups which can be cleaved. Cleavage of the two phosphate bonds of the bi-indoxylphosphate will create a bi-indoxyl molecule which will dimerize with two other bi-indoxyl molecules, and so on, to create a self-assembling linear polymer. The attachment of the two indoxylphosphates can be either direct or indirect via a digestible or non-digestible spacer molecule as illustrated in FIG. 15. The spacer molecule itself can have antigenic epitopes and can be one of several kinds of molecules such as a poly (ethylene oxide) polymer with hetero-bifunctional reactive groups at its terminals (Yokoyama et al, 1992, Bioconjug. Chem. 3, 275–276), a non-degradable copolymer [N-(2-hydroxypropyl) methacrylamide] which is non-immunogenic and has a versatile chemistry which allows for a range of side chains and pendant chemicals such as lactose, mannose, and radio-labeled tyrosinamide. Such molecules have antigenic epitopes and can be introduced to add an additional antigenic epitope to the spacer (Maeda et al, 1992, Bioconug, Chem. 3, 351–362; Seymour, 1992, Critical Reviews in Therapeutic Drug Carrier Systems, 9, 135–187; Primm et al, 1993, J. Drug Target. 1, 125–131) and a hydrophobic hexamethylene spacer group (Ouchi et al, 1992, Drug Des. Discov. 9, 93–105). The formation of the precipitate in the form of an insoluble linear polymer has substantial advantages in reducing the ability of the precipitate to diffuse or move with the convective flow of fluids. In addition, the various antigenic epitopes on the linear polymer can be spaced in an ordered fashion to reduce steric hindrance of antibodies or peptides which can bind to any of the antigenic epitopes (the antigenic epitopes including the first antigenic epitope on the precipitate, the second antigenic epitope on the precipitate, the neo-antigenic third epitope of the indigo precipitate, the antigenic epitopes on the spacer molecule, and the antigenic epitopes on chemicals attached to the spacer molecule).

Additional indoles can be made by attaching chemicals to them at various positions. For example, (a) glycosides can be attached at position 3 to form indole glycosides, the glycoside can be one of cellobiose which cannot be cleaved by mammalian enzymes and which can be cleaved by a non-mammalian enzyme, (b) all substituents at position 4, 5, 6, and 7, including hydroxyl groups, (c) phenyl at position 5, and all its derivatives, (d) benzyloxy at position 5 and all its derivatives, and (e) 5,5-bi-indoxyls, with or without spacers.

The indoxyl can also be radio-labeled with radio iodine or other radio-isotopes. Radio-iodination of the indoxyl compounds can be achieved in three ways: (1) FIG. 16 shows parahydroxy Benzyl Ether of 5-Hydroxy-indoxyl phosphate is radio-iodinated, (2) FIG. 17 shows indoxyl with a para-hydroxyphenyl substituted at the 5 position is radio-iodinated, and (3) FIG. 18 shows the starting material, 1-acetyl-5-iodo-3-hydroxyindole, which is treated with radioactive iodine in 3M HCL. After warming for about 30 minutes, the iodoindole is re-isolated, now containing radioactive iodine. To prepare the tritium labeled compound, the corresponding indole is treated with tritiated water under acid conditions in teterahydrofuran. The indole is re-isolated, in which the aromatic hydrogens have been replaced in part by tritium.

The indoxyls can also be heavily radio-labeled so that when the indoxyl accumulates as a precipitate in the targeted cells, the radio-isotopes of the precipitate will generate a radiation field that will extend beyond the cell that had accumulated the precipitate and kill non-selectively the cells adjacent to the targeted cells that have accumulated the precipitate. The number of isotope atoms that accumulate as a precipitate in targeted cells can be very large because the number depends on the amount of precipitate that has accumulated, and, for reasons described above, the amount of accumulation can be made as large as desired. Because the precipitate is stable and accumulates and remains in the cell for an extended period of time, the long residence time of the isotope, combined with the large number of isotope atoms which can be made to accumulate, will generate a supra-lethal field of radiation, i.e. Hot-Spot, in the immediate micro-region around the targeted cells that had accumulated precipitate. As described, indoxyls that have been heavily radio-labeled can be used as therapeutic agents to treat different disease states including cancer. For example, as applied to the treatment of cancer, the use of heavily radio-labeled indoxyls cause the generation of Hot-Spots around targeted cells thereby circumventing the need for every individual cancer cell to be targeted and accumulate precipitate in order for all the cancer cells to be killed.

There are four methods of attaching the soluble indoxylphosphate to the protein or peptide targeting agent covalent bonding, covalent acid labile bonding, non-covalent Van Der Waal forces, and ionic bonding.

Covalent bonding of indoxylphosphate to protein targeting agent is one method of attaching the soluble indoxylphosphate to the protein or peptide targeting agent. In the prior art, it is known that a large number of soluble drugs, antidotes, toxins, dyes, carbohydrates, and other chemicals, have been covalently attached by numerous methods to targeting proteins (Pittman et al. 1983, Biochem. J. 212, 791–800; Mukhopadhyay and Basu 1990, Biotechnology and Appl. Biochem. 12,529–536; Ali et al. 1990, Cancer Research Suppl. 50, 83–788: Zhong et al., 1992, Biochimica. et Biophysica Acta, 1106, 311–316; O'Hare et al. 1993, J. Drug Target 1, 217–219). The attachment of the targeting agent to the soluble chemical is relatively stable in the extra-cellular fluid so that the attached chemical is mainly released in the lysosome of targeted cells. The attachment of the chemicals to the targeting agent can be achieved without interfering with the binding ability of the targeting agent, or with the function of the chemical after it is detached. In fact, the function of the detached chemical can be maintained even though an amino-acid or peptide "tail" remains attached to the chemical after the main part of the protein has been digested (Novak-Hofer et al, 1995, Cancer Research, 55, 46–50; Duncan and Welch, 1993, J. Nuclear Med. 34, 1728–1738).

In accordance with the invention, the first targeting agent, being the first moiety of the binary reagent can be covalently attached to the soluble indoxylphosphate which is the second moiety of the binary reagent to make the binary reagent The attachment can be made either at the benzene or pyrrole ring of the indoxylphosphate by a lysosomal enzyme and/or acidic sensitive link. When a critical amount of the targeting protein has been digested by the lysosome enzymes, or when the link between the targeting agent and the indoxylphosphate has been digested, and after the phosphate of the indoxylphosphate has been cleaved by acid phosphatase, free indoxyl molecules will be formed which will readily oxidize. Once in the oxidized form, the indoxyl will spontaneously dimerize to form the highly insoluble indigo dye which will, rapidly and spontaneously precipitate without the need for further enzyme action. Indoxylphosphate can be covalently attached to protein targeting agents in the following ways.

1. The first method of attachment is at site (a) and it can be achieved by to the 3-indoxyl phosphate (0.1 m. mol) in tetrahydrafurn (10 ml) is added excess thionyl chloride (10 m. mol) and the solution is warmed to 40 degrees Celsius and kept at that temperature for thirty minutes. It is then evaporated in a rotary evaporator, tetrahydrofuran is added, and then the evaporation repeated. The residue is dissolved in tetrahydrofuran (2 ml) and added to the protein (25 mg.) dissolved in 10 ml of water buffered at pH 7. The mixture is stirred at room temperature for 30 minutes, then lyophilized to cleave the 3-indoxyl phosphate covalently bound to the protein. This material is suitable for addition to the cells.

2. The second method of attachment is at site (a) using a different process from the first method. To the 3-indoxyl phosphate (0.1 m. mol) in water (3 ml) is added the water soluble dimide, 1-(3-dimethylaminopropyl)-3-ethylcarbodimide hydrochloride (0.11 m. mol) in water (2 ml). The solution is stirred at room temperature for 5 minutes and then added to a solution of the protein (25 mg) in 5 ml of water. The resulting solution is warmed to 35 degrees Celsius, kept at that temperature for 10 minutes, then cooled to 20 degrees Celsius. Reverse-phase chromatography, eluting with water-acetonitrile- 1% trifluoracetic acid, gives the pure, covalently bound 3-indolyl-phosphate-protein. Coupling also can be effected by using a linker between the 3-indolyl-phosphate and the protein. This alternative is illustrated in the third method.

3. The third method of attachment is also at site (a). Following the protocol of the first method, the 3-indoxyl phosphate (0.1 m. mol) is converted to the corresponding phosphoryl chloride, which is obtained as the final solution (see first method) in tetrahydrofuran (5 ml). This solution is added to 3-aminopropionic acid (0.1 m. mol) dissolved in water (5 ml), and the mixture is warmed to 50 degrees Celsius for 30 minutes. Evaporation and chromatography on silica, normal phase, gives the B-(3 indolylphosphoryl) aminopropionic acid. This propionic acid is dissolved in water (5 ml), treated with 1-(3-dimethylaminopropyl)-3-ethylcarbodiimide in water (3 ml) in 10 ml of water. Coupling is allowed to proceed for one hour. The solution is then lyophilized and the residue is purified by reverse phase chromatography. The product isolated is the 3-indolyl phosphate linked to the amino group of 3-aminopropionic acid, in turn linked via its carboxylic acid group to the free amino acid groups of the protein.

4. The fourth method of attachment at site (c). In this example, the phosphate group is present as the dibenzyl ester and the substituent on the benzene ring is carboxy. This molecule is treated in Example 2 to form an amide bond with the protein. The phosphate benzyl esters are then converted to phosphate by hydrogenolytic conditions.

An alternative method is covalent, acid labile bonding of indoxylphosphate to the protein targeting agent. Various protein targeting agents have been attached to drugs such as 5-Iodo 2-deoxyuridine phosphate (Biessen et al. 1994, J. of Hepatology 21, 806–815) and acyclovir monophosphate (Fiume et al. 1989, Naturwissenschaften, 76, 7476) via a phosphamide link which is acid labile. The drug phosphates were released in the acidic, enzyme rich environment of the lysosome of cells.

In accordance with the invention, indoxylphosphate attachment to the targeting agent by a phosphamide linkage between indoxylphosphate and lactosylated polylysine or protein is effected using 3-aminopropionic acid as in example C. First the beta-(3-indolylphosphoryl) aminopropionic acid is formed and this is coupled to the lactosylated polylysine, polylysine, or protein as described.

Initial cleavage can be at the indoxyl phosphate bond to directly form the indoxyl which spontaneously precipitates. Initial cleavage can be between the phosphate and amino group which liberates indoxyl phosphate which must then be cleaved to indoxyl. Initial cleavage can be at the protein bond liberates beta-(3-indolylphosphoryl)aminopropionic acid which will then undergo further cleavage to indoxyl or indoxylphosphate.

Direct covalent coupling of antibodies to the soluble precipitable material has some potential disadvantages. For example, the chemical manipulations necessary to make the coupling can (a) reduce or even destroy the specific binding ability of the targeting agent, (b) alter the distribution of the binary reagent in the body, or (c) alter the attached precipitable material which could prevent final precipitation from occurring. In addition, precipitation of the precipitable material will also not occur if the covalent bond between the carrier targeting agent and the precipitable material is not cleaved or if an amino-acid or peptide "tail" remains after partial digestion of the targeting agent. For these reasons, the precipitable material has also been attached to the targeting agent by noncovalent Van Der Waal and ionic forces; however, non-covalent bonding has the disadvantage of not being as stable as the covalent linkage. As a consequence of this less stable linkage, the attached precipitable material can disassociate from the targeting agent in the extra-cellular fluid and precipitate prior to (and instead of) precipitating after it has been transported to the lysosomes by receptor mediated endocytosis.

The attachment of the targeting agent can also be achieved by non-covalent antibody or peptide binding to indoxylphosphate by Van Der Waal forces. It is known that a large number of soluble molecules have been bound to their matching antibodies to form soluble binary reagents. This method can be used to form the soluble first binary reagent comprised of indoxylphosphate or other soluble precipitable materials and their matching targeting agent. However, in order for the first binary reagent to both target the first target cells and carry the indoxylphosphate, the first binary reagent must be made using a bispecific reagent having two different binding domains. One domain of the bispecific reagent must be able to bind to the endocytosing receptor on the first target cells. The other domain of the bispecific reagent must be able to bind to the indoxylphosphate or other soluble precipitable material. The bispecific reagent can be made by published biological methods (Kohler and Milstein, 1975, Nature, 256, 495–497; Milstein and Cuello, 1983, Nature, 305, 537–540; Webb et al, 1985, Cancer Treatment Reports, 69, 663–672; Suresh et al. 1986, Proc. of the Nat. Acad. Science USA., 83, 7989–7993; Tiebout et al. 1987, J. of Immun. 139, 3402–3405; Umovitz et al. 1988, J. of Immun. 140, 558–563); chemical methods (Nisonoff and Rivers, 1961, Arch. of Bioch. and Biophys., 93, 460–462; Karpovsky et al. 1984, J. of Expt. Med; 160, 1686–1701; Brennan et al., 1985 Liu et al., 1985, Proc. of the Natl. Acadm. Science USA., 82, 8648–8652; Lansdorp et al., 1986, European J. of Immunol. 16, 679–683; Glennie et al. 1987, J. of Immun., 139, 2367–2375); and genetic engineering methods (Morrison et al., 1984, Proc. of the Natl. Acad. of Sciences USA., 81, 6851–6855; Boulianne et al., 1984, Nature, 312, 643–646 1984).

When the binary reagent binds to the receptor on the target cells, it induces receptor mediated endocytosis which transports the binary reagent to the lysosomes. The soluble indoxylphosphate is cleaved and freed from its binding to the targeting agent moiety of the binary reagent by the acidic environment of the lysosomes, aided by an esterase or peptidase which partially or completely digests the protein portions of the binary reagent. The phosphate bond is cleaved by the acid phosphatase in the lysosomes. The cleavage of the phosphate liberates an indoxyl which spontaneously dimerizes and forms a new molecule which is insoluble and precipitates as an indigo dye having a neo-antigenic third epitope not present on the indoxylphosphate or the intermediate molecules which are created prior to forming the insoluble indigo.

The fourth method of attachment is via ionic binding protein targeting agent to indoxylphosphoric acid. Since polylysine is basic, it can be attached to chemicals, like indoxylphosphoric acid, to make a salt. This method has been used to attach DNA, antisense DNA, and other nucleotides to polylysine as a step towards targeting these nucleotide reagents to specific cells.

Figure 19:
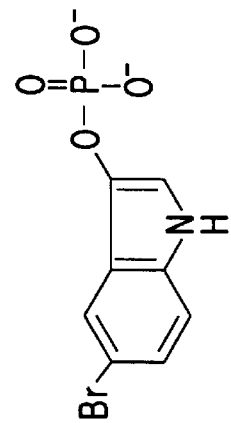
FIG. 19 shows salt of polylysine and indolphosphoric acid.
Figure 19:
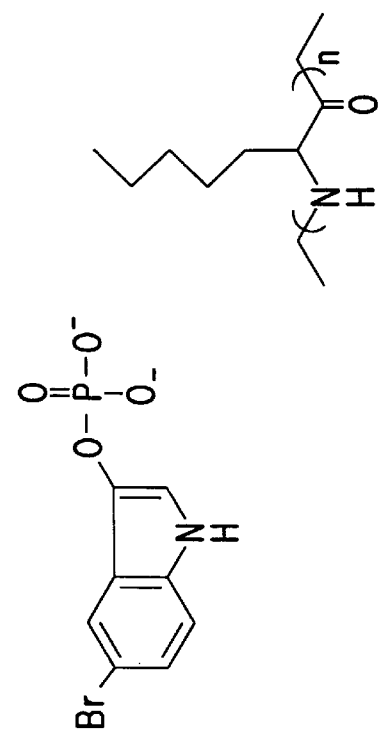

In accordance with the present invention, the ionic method was used to deliver indoxylphosphoric as a salt of lactosylated polylysine to liver cancer cells by making a simple poly-L-lysine 5-bromoindoxl phosphate conjugate. Poly-L-lysine HBr salt with a molecular weight of 5000–15000 (average molecular weight 8000 by LALLS, 9600 by viscosity), was run through an anion exchange column (Dowex 2 -x, 50–100 mesh, OH form generated from Cl form) to remove the toxic bromide anion. After the combined ninhydrin positive fractions were mixed with a solution of indoxylphosphoric acid in EtOAc and MeOH, a precipitate was formed immediately, which was insoluble in water and other organic solvents. FIG. 19 shows the chemical structure of the salt of polylysine and indoxylphosphoric acid.

No water soluble product was obtained when the ratio of indoxyl phosphate to poly-L-lysine was changed gradually from 5 mol %: 100 mol % (based on lysine residue) to 50 mol %: 100 mol %. While an increasing solubility of bromo-indoxyl was observed in the presence of NaCl, a large amount of NaCl was necessary to dissolve bromo-indoxyl in the solution (10 mg of bromo-indoxyl in 10 ml of 0.5M NaCl) and thus this method was impractical.

Figure 20:
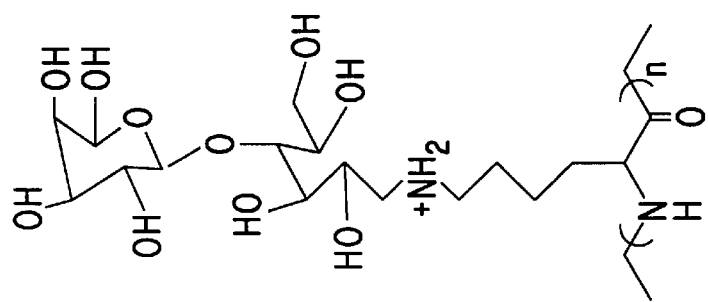
FIG. 20 shows salt of indoxylphosphoric acid and lactosylated polylysine.

Lactose residues on the poly-L-lysine molecule increase the solubility of its conjugates. It was applicable to our system. As shown in FIG. 20 poly-L-lysine was lactosylated with sodium cyanoborohydride at pH 5.0 to form the acetate of lactosylated-polylysine. A solution of free lactosylated polylysine in water was mixed with phosphoric acid in EtOAc and MeOH solution and the final product was a water soluble white solid. A higher molecular weight poly-L-lysine, with a molecular weight of 15000–30000 (average molecular weight 18000 by LALLS, 19200 by Viscosity) was treated under the same procedure. The final product was still soluble in water, but the solubility was less than that of the product made with the polylysine of lower MW.

The hepatoma cell line, HepG2, which is known to have the specific asialoglycoprotein receptor was grown in tissue culture medium. Because it was found that fetal calf serum contained phosphatase enzyme which reacted with the lactosylated polylysine-indoxylphosphate to cause indigo to precipitate in the medium, the cells were grown in the absence of fetal calf serum. Experiments showed that under these conditions, and in the absence of the HepG2 cells, precipitation did not occur. The HepG2 cells were cultured in duplicate cultures for 5 days in plastic ware (Falcon) at 37 degrees centigrade under 5% carbon dioxide and 95% air in medium, containing 5 milli-molar concentration of the lactosylated polylysine-indoxylphosphate. At the end of the culture period, the cells were washed 3 times in balanced salt solution and harvested. The cells were incubated with 0.1 normal sodium hydroxide for 30 minutes at room temperature, then dissolved in liquid scintillation fluid, and finally centrifuged in 2 ml. centrifuge tubes. The indigo blue precipitate was seen as a small pellet made up of small particles approximately 0.1 micron in diameter.

The lactosylated polylysine acts as a specific ligand for the asialoglycoprotein receptor of normal and malignant liver cells. Therefore, for this ligand-cell system, there is no need for a targeting agent to be attached to the lactosylated polylysine. However, in the more general case, a targeting agent would be covalently attached to the polylysine component of the salt to make a binary reagent (Lu et al. 1994, J. of Nuclear Med. 35, 269 275). It is thought that this latter method can allow for the attachment of a large number of drugs to the polylysine without interfering with the binding ability of the protein targeting agent.

The method of carrying the soluble precipitable material to the lysosomes of targeted cells by non-covalent binding, via a bispecific antibody reagent or ionic binding has some advantages over covalent bonding. Bispecific antibodies are structurally bivalent but functionally univalent for each antigen binding site. The univalent attachment of the antibody to the cell receptor, compared to the attachment of bivalent antibodies, minimizes antigenic modualtion (Glennie et al., 1988, J. of Immunol., 141, 3662–3670). One manifestation of modulation being a loss of binding sites (Gordon and Stevenson, 1981, J. of Immunol., 42, 13–17: Cobbold and Waldmann, 1984, Nature, 308, 460 462). Non-covalent bonding also does not chemically alter the indoxylphosphate and does not interfere with the binding ability of either of the two binding sites of the bispecific antibody. Non-covalent binding allows the indoxylphosphate to be easily detached from the antibody or peptide to which it was bound. The detachment process cannot leave an amino-acid or peptide "tail" on the detached indoxylphosphate which might otherwise interfere with the subsequent ability of the phosphatase enzyme to cleave the phosphate bond to form the indoxyl and to precipitate. However, non-covalent bonding has the disadvantage that the bonding is not as stable as covalent bonding and can disassociate in the body fluids prior to its transport to the targeted cells and prior to its receptor mediated endocytic transport into the lysosomes of the targeted cell.

Other soluble chemicals can be attached to the targeting agent. When these other chemicals are detached and free, they can polymerize oxidatively, thermally, or photochemically to form an insoluble chemical which precipitates. For example strategically substituted porphyrins can be photochemically polymerized; 5,6-dihydroxyindole oxidatively polymerizes to form insoluble melanin and phenothiazines can be converted to insoluble methylene blue-like molecules.

Figure 21:
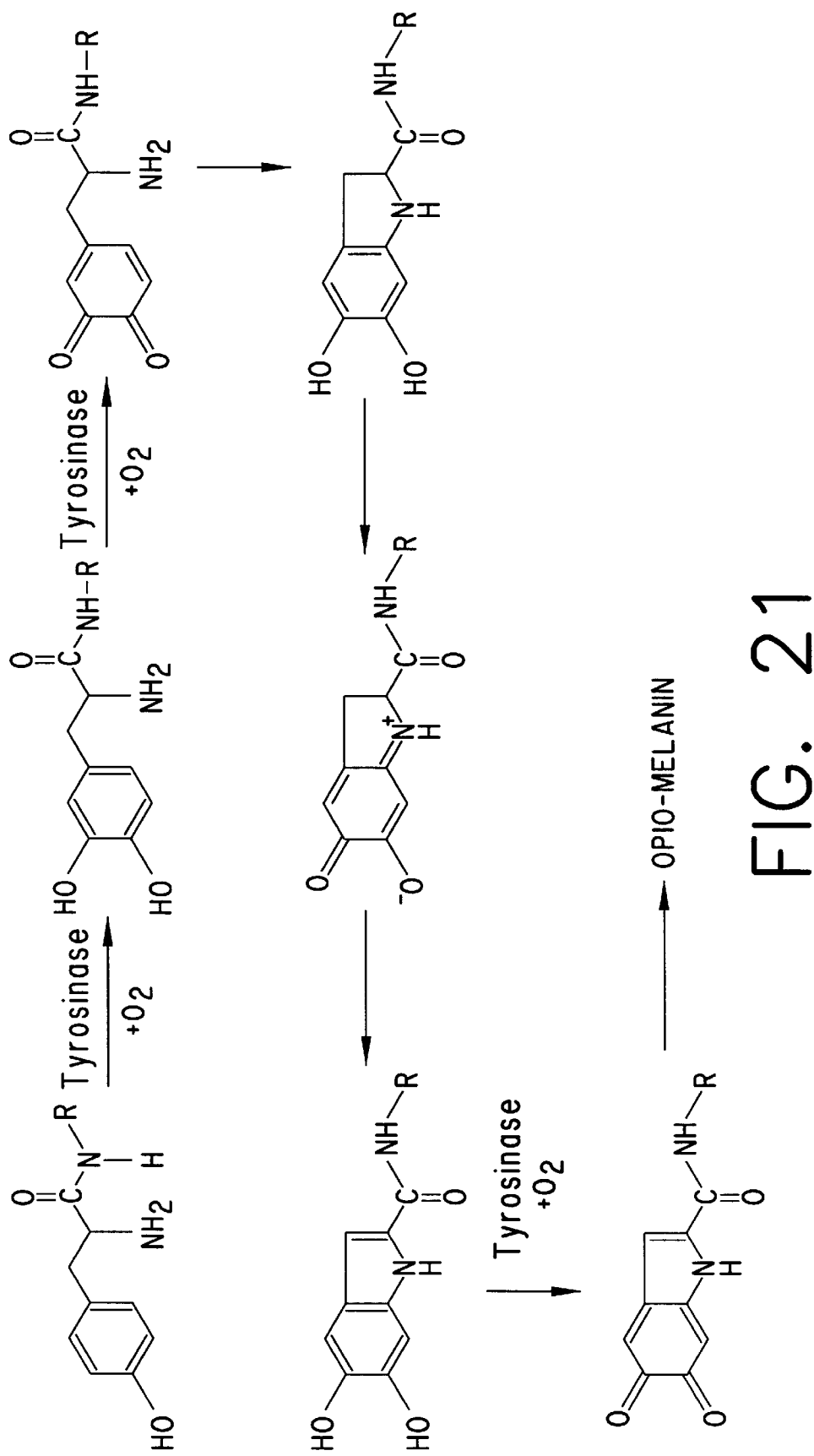
FIG. 21 shows the steps leading to the synthesis opiomelanin.

A further method of making a soluble precipitable material includes a method in which a domain of a soluble peptide or amino-acid moiety of a soluble peptide is converted into an insoluble material, the peptide remaining soluble because of the solubilizing effect of the unchanged peptide moiety. However, if the unchanged peptide moiety is digested, the converted material being insoluble will precipitate. FIG. 21 is an illustration of a specific example of such a system. The Mason-Rapier pathway for the ofrmation of opio-melanins by the tyeosinase-catalyzed oxidation of opiod peptides, where R represents the peptide chain, where the use of opioid peptides which can be converted by mushroom tyrosinase into melanin-like compounds, retaining the peptide moiety to make opio-melanins which are soluble owing to the presence of the linked amino-acids (Rosei et al 1991, Biochem. Biophys. Res. Commun. 179, 147–152). The soluble enkephalin-generated melanins can be covalently attached to the targeting agent in aqueous medium and when the targeting agent is digested and/or the opio-peptide is cleaved by carboxypeptidase A, an insoluble melanin like material is released and precipitates. Enkephalins as well as other opioid peptides including alpha-endorphins, kyotorphin and esorphins, if oxidized in the presence of DOPA and tyrosinase, are readily incorporated into DPOA-melanin. The resulting mixed melanins, opio-melanin plus DOPA-melanin, in contrast to the first example are insoluble and can be solubilized in hydrophilic solvents (Rosei et al 1994, Biochemica et Biophysica Acta, 1199, 123–129), and attached to the targeting agent in this medium. After the targeting agent and enkephalins are digested, the mixed melanins are released as an insoluble material which will precipitate. An advantage of these materials is that they can be made as fusion proteins by genetic engineering which avoids the necessity of attaching the targeting agent to the precipitable material.

Another alternative method of accumulating a precipitate in first target cells is when the soluble precipitable material comprises two soluble chemicals being a third and fourth soluble chemicals, each chemical being attached to a targeting agent, the targeting agent being the same for each of the soluble chemicals, the two soluble chemicals, being detached from the targeting agent by at least one of the lysosome enzymes, react with each other to form a precipitate within the targeted cells. An example of two such soluble precipitable chemicals is the precipitation which occurs when two oppositely charged synthetic linear water-soluble polyelectrolytes, poly-N-ethyl-4-vinyl-pyridine as the polycation reacts with polymethacrylate as the polyanion (Dzantiev et al, 1994, Immunology Letters, 41, 205–211). Another example is the attachment of both an easily oxidized substance, such as polyphenol and a peroxide, to the same targeting agent so that both functions are blocked. Digestion of the targeting agent then liberates both functions which react with each other and form insoluble substances.

Accumulation of a precipitate in first target cells can also be achieved by introducing into the first target cells a binary reagent where the soluble precipitable material, being detached from the targeting agent, reacts with a product produced endogenously by the first target cells to produce an insoluble, relatively non-digestible complex. Tilorone, acridine orange, and other substituted dicationic compounds induce the accumulation in lysosomes of the complex formed by the reaction between tilorone, acridine orange and other substituted dicationic compounds and the endogenously produced glycosaminoglycans by forming insoluble complexes which are relatively non-digestible by glycosidases and which precipitate in the lysosomes (Lullmann-Rauch R. et. al 1995, Biochem. Pharmacol. 49, 1223–12333; Fischer J, 1995, Biochem. J. 312, 215–222). In a similar way, amiodarone complexes to phospholipids and causes the accumulation of the relatively non-digestible and insoluble amiodarone-phospholipid complex. A linear correlation exists between the cellular amiodarone levels and phospholipid accumulation suggesting a stoichiometric relationship and D-alpha-tocopherol (vitamin E) reduces the accumulation of the amiodarone induced accumulation of the phospholipid (Honegger U. E. et al, 1995, Biochem. Pharmacol. 49, 1741 1745; Palmeri S et al., 1995, Life Sci., 57, 1963–1971).

The second class of soluble precipitable materials are composed of a soluble moiety attached to an insoluble moiety. It is known that the covalent and non-covalent attachment of small insoluble molecules to proteins, polymers, or conjugates of proteins and polymers can solubilize the otherwise insoluble chemicals. The solubilizing process is illustrated by the following examples. Specific plasma proteins are known to solubilize and carry a variety of relatively insoluble molecules such as steroids, vitamins and other substances in the blood and to release them at the target site. For example, free carotenoids are insoluble in aqueous medium, but non-covalent complexes of carotenoids with protein are soluble and stable over a the pH range 5.0 to 8.5 (Zagalsky P. 1995, Carotenoids Volume 1A, Isolation and Analysis, Birkhauser Verlag Basel P. 287–230). Covalent conjugates of albumin with poly (alkylene oxide) solubilize the otherwise insoluble riboflavin ester benzaflavin (Topchieva et al. 1993, Biotechnology Appl. Biochem. 17,337–348).

The second class of soluble precipitable material has a soluble moiety attached to an insoluble moiety, and being soluble in aqueous medium this class of soluble precipitable material can be attached to a protein targeting agent by conventional methods to make a soluble binary reagent. The second class of soluble precipitable materials can be made by two methods. In the first method, the aqueous insoluble moiety is attached to the soluble moiety in an organic solvent in which both the aqueous soluble moiety and aqueous insoluble moiety are soluble and stable, the complex material being aqueous soluble and being the soluble precipitable material. In the second method, the aqueous insoluble moiety is first treated while it is an insoluble substance, or in an organic solvent while in solution to remove the insolubilizing groups, to become an aqueous soluble material. The organic solvent is replaced with an aqueous medium and the now soluble material is attached to the soluble moiety to make a soluble material which is treated chemically or enzymatically to replace the insolubilizing groups without markedly reducing the aqueous solubility of the treated material, which is now the soluble precipitable material and can be attached to the targeting agent to make a soluble binary reagent. The formation of a precipitate from the second class of soluble precipitable material requires an enzyme in the lysosomes and/or the acid environment in the lysosomes of the first target cells to detach the soluble non-toxic precipitable material from its attachment to the targeting agent. The detached soluble precipitable material is acted on by an enzyme in the lysosomes and/or the acid environment of the targeted cells to detach the soluble moiety of the soluble precipitable material from its attachment to the insoluble moiety thereby causing the insoluble moiety to precipitate. The detachment of the insoluble moiety can be achieved by three methods. In the first method an enzyme in the lysosomes digests the soluble moiety of the soluble precipitable material thereby dissipating the solubilizing effect of the soluble moiety, the remaining material being an insoluble material spontaneously precipitates. In the second method an enzyme in the lysosomes cleaves the soluble moiety thereby eliminating the solubilizing effect of the soluble moiety, the remaining material being insoluble spontaneously precipitates. In the third method the soluble moiety of the soluble precipitable material is attached to a peptide moiety with a substantial affinity for the insoluble moiety and when the peptide moiety of the soluble moiety is partially digested by enzymes in the lysosomes of target cells, the binding affinity of the peptide moiety of the soluble moiety is dissipated thereby detaching the soluble moiety and eliminating the solubilizing effect of the soluble moiety, the remaining material being insoluble spontaneously precipitates.

The choice of the insoluble, small, non-digestible molecule could have a broad range and include porphyrins, alkaloids, polynuclear compounds, insoluble carbohydrates, and natural and synthetic polymers.

A specific example of the second method of dealing with an insoluble precipitable material is the application of chitin, (as an example of X+Y). Chitin is a highly insoluble molecule even when it has a low degree of polymerization (DP). Chitin can be solubilized by enzymatically or chemical deacetylation (removing Y) to form chitosan (X). Chitosan, a copolymer derived from the abundant natural polymer chitin, is composed of 2-amino-deoxy-D-glucose and 2-acetamide-2-deoxy-D-glucose units. Chitosan is soluble in water and can be depolymerized by nitrous acid (G. Graham Allan and Mark Peyron 1995, Carbohydrate Research, 277,257–272) and by the action of chitinase (Usui T. et al. 1987, Biochim. Biophys. Acta, 923, 302–305) to generate oligomers of any required size. The soluble chitosan (X) with a degree of polymerization of 10–14 can be attached by conventional means in aqueous medium to a polymer of polyproline (P) of sufficient molecular size. The complex material (X+P) can be derivatized with acetic anhydride, without derivatizing or affecting the solubilizing effect of the acetic anhydride-resistant polyproline (P). The acetic anhydride re-acetylates the complex (adds Y to the chitosan component of the complex material) to form a chitin which remains soluble because of its attachment to the unchanged hydrophilic polyproline. The chitin material (X+Y) will remain soluble even though the chitosan (X) component of the material has been converted to chitin (X+Y) because of the solubilizing effect of the unchanged hydrophilic polyproline (P). The soluble precipitable material attached to the polyproline (X+Y+P) can now be attached to the targeting agent by conventional means in an aqueous medium to form a soluble binary reagent The soluble binary reagent is transported by receptor mediated endocytosis to the lysosomes of the targeted cells. After the attached solubilizing polymer and targeting agent have been sufficiently digested by lysosomal enzymes, or after the bond between the chitin and the attached solubilizing polymer and targeting agent has been cleaved, their solubilizing effect will be dissipated, and the chitin portion of the binary complex, with or without an amino-acid or peptide "tail" left after the incomplete digestion of the targeting agent, will return to its insoluble state, and being insoluble and non-digestible, the chitin precipitates without the need for further enzyme action. Modifications of the chitin can be made to achieve certain characteristics. For example, chitin, can be made more aqueous soluble and more easily digested by mammalian and non-mammalian enzymes by a lower degree of chitosan acetylation.

Another specific example of an insoluble precipitable material is cellulose which is a linear polymer of anhydroglucose units linked by beta-1-4-glycosidic bonds. Insoluble microcrystalline cellulose can be converted into cello-oligomers of different sizes or different degrees of polymerization or DP (Kieman et al. 1994, Biochem 3021 463–469). Non-catalytic cellulose binding proteins (CBD) of MW 10,000 to 15,000 have been isolated and characterized. The gene coding for this peptide has been isolated and inserted into the genome of several cell types so that large quantities can be harvested. The CBD binds, virtually irreversibly, by Van Der Waal forces to high DP (degree of polymerization) cellulose and with a lower affinity to cellulose as small as 5 DP (Tomme P et al 1994, Protein Engineering, 7,117–123; Ferreira L. M. et al., 1993, Biochem. J. 204,349–355).

Celluloses with a DP of 7–10 are highly insoluble in water but are soluble in DMSO. CBD can bind to cellulose of DP 7–10 in DMSO. A complex of a solubilizing polymer covalently attached to the CBD will also bind to a small DP cellulose in DMSO to create a soluble complex (cellulose+ CBD+solubilizing polymer). After creating this complex in DMSO, the DMSO can be replaced with an aqueous medium, and the now soluble complex can be covalently attached in an aqueous medium to the protein targeting agent, by conventional methods, to form a soluble binary reagent. The soluble binary reagent can be administered to the living host and will bind to the receptors on targeted cells. After receptor mediated endocytosis and lysosomal enzyme processing, the CBD is partially or completely digested which will release the small insoluble molecule of cellulose which will immediately precipitate and again has the ability to bind to the CBD peptide. Any cellulose or chitin which forms a precipitate in the extra-cellular fluid without having been endocytosed inside cells can be digested by the administration of the appropriate cellulase or chitinase enzyme. The digestion of the cellulose or chitin is analogous to the digestion of fibrin by the administration of tissue plasminogen activating factor.

Another specific example of an insoluble precipitable material is the thermo-reversible polymer of poly (N-isopropylacrylamide) which has been synthesized with carboxyl functional end groups. The polymer is soluble below a critical temperature, and at this temperature, it can be attached in aqueous medium to the targeting agent by conventional methods, to produce an aqueous soluble binary reagent (Chen and Hoffman 1994,5,371–382). A small increase in temperature causes the polymer to become insoluble, but the binary reagent will remain soluble by the solubilizing effect of the targeting agent with or without the aid of an attached solubilizing polymer such as polyethylene glycol. The soluble binary reagent can be delivered to the lysosomes of targeted cells where the solubilizing effect of the targeting agent and solubilizing polymer will be dissipated and the thermo-reversible polymer will precipitate.

The exemplary examples outlined above are directed towards achieving the accumulation and trapping of a relatively non-digestible precipitate in the lysosomes of targeted cells. In all these cases the primary requirements are that the carrier targeting agent to which the precipitable material is attached be recognized by, and will bind to the targeted receptors like the native protein, and there is adequate accumulation and retention of the precipitate in the targeted cell, with virtually zero redistribution of the precipitate to non-targeted cells.

The present invention may be applied to a wide range of medical and biological uses including diagnostic scanning of patients for illnesses such as cancer, testing the specificity of targeting agents, providing real-time information to assist in tumor surgery, therapy for cancer, as a research tool to study ligand-receptor relationships, and the specificity of ligands administered at physiological and pharmacological levels.

Conventional methods of diagnostic scanning use targeting agents like radio-labeled antibodies, which binds to antigenic receptors on targeted cells. Since there is a fixed number of antigenic receptors on the cell, a number which is relatively low, only a low number of isotope atoms will bind to the cell. Moreover, the radio-labeled antibody only remains bound to the cell for a short time, making it necessary to perform the scan at a time when radioactive molecules are still in the circulation which creates a relatively high radioactive background. The low number of bound isotope atoms together with the high radioactivity in the background reduces the precision of the picture obtained by the scan.

The present invention can be used for diagnostic scanning for cancer by administering a soluble binary reagent to the subject, the first moiety of the binary reagent being a targeting agent having a substantial affinity for the antigenic receptors on certain cell types such as cancer cells, the second moiety being a trace labeled soluble precipitable material. The binary reagent binds to the antigenic receptors on the target cancer cells, the binding causing the cell to endocytose the binary reagent, the endocytosis and lysosome enzymes detaching the trace labeled soluble precipitable material and converting the detached soluble precipitable material into an insoluble material which precipitates and accumulates in the lysosomes of the cell, the accumulated precipitate remaining in the cell for an extended period of time.

After the level of radioactivity in the body fluids has fallen to insignificant or zero levels, the fall to this low level having occurred by the host's natural elimination system and by the lapse of time, the living host can be scanned by an external piece of equipment which detects radioactivity, thereby enabling the trace-labeled precipitate in the targeted cells to be imaged, thereby enabling the targeted cells containing the precipitate to be imaged. More specifically, antibodies, antibody fragments or derivatives of antibodies, specific for a tumor antigen, can be coupled to the trace labeled chemical agent and the product so produced can be used to image tumors and metastasizing growths.

Since tracelabeled precipitates which have accumulated in the lysosomes of mammalian cells are retained in this compartment virtually for the life of the cell, a number of advantages can be gained. In method of the present invention, by continuing the administration of the binary reagent for a sufficiently long period of time, a large amount of trace labeled precipitate can be made to accumulate. Since the accumulated trace labeled precipitate remains in the cell for an extended period of time which enables the scan to be carried long enough after the administration of the binary reagent has been completed for the radioactivity in the body fluid to fall naturally to a negligible or zero level. The large number of isotope atoms in the targeted cells together with the zero background of radioactivity enables the picture obtained by the scan to be very clear and sharply demarcated. The sharply demarcated picture on the scan enables the edges of the demarcated picture to be seen as rough or smooth, the sharp demarcation providing information which enables more correct interpretations of the picture to be made in order to make a correct diagnosis.

The clear and retained picture of the radioactive precipitate obtained by the scan can be used at a later time to perform a second scan for accurate comparison between the first and second scan. The accumulated precipitate will still be present at a later time and, even though the radiation level would have physically decayed, there will be sufficient radiation at the time of the second scan to position the host in the same position with respect to the scanning equipment as the first scan. The accurate positioning enables an accurate comparative second scan to be made. An enlarging lesion, as determined by an enlarging region of radioactivity in the second scan, is a much better diagnostic sign for many lesions, especially cancer, than a single static picture. A lesion diminishing in size suggests that the lesion is not malignant.

The method of diagnostic scanning of the suspect area and of selected normal tissues can be followed by a biopsy sample of the suspect lesion and selected normal tissue, the tissues being examined histologically and by radioautography and an estimate of the location, frequency, distribution of the cells which have accumulated the trace labeled precipitate can be made. This information can be used to plan the therapy regimen of various therapeutic modalities, such as treatment of cancer by immunotoxins. Currently, immunotoxin therapy methods use an immunotoxin in which the targeting agent moiety of the immunotoxin is selected by the clinical diagnosis of the type of cancer. However, it is well known that cancer cells in different subjects with the "same" clinically diagnosed type of cancer have different antigenic receptors, therefore, this method of selecting the targeting moiety results in serious error which leads to subjects receiving high doses of the immunotoxin which are inappropriate for the particular cancer in any one individual. Another method of selecting the targeting moiety of a candidate immunotoxin for a particular subject is to remove a sample of the subject's tumor by biopsy and grow the cells in tissue culture. A great variety of culture methods have been developed in an attempt to make the results from examination of cultured cells a valid measure for their successful in vivo use. However, the results from such studies have not been very successful because cells in tissue culture change their receptor repertoire quickly and dramatically. Testing targeting agent by in vivo test, as can be carried out by the method of the present invention, is a more valid method than an in vitro test.

A diagnostic scan carried out by the method of the present invention enables an accurate prediction to be made as to whether the selected immunotoxin will be of therapeutic value, prior to the administration of the toxic amount of the candidate immunotoxin.

The method of the present invention can be used in conjunction with surgical removal of a tumor. A binary reagent, composed of a selected targeting agent attached to a trace labeled soluble precipitable material, is administered to the living host prior to the surgical procedure to remove the tumor. After the radioactivity in the body fluids has reached insignificantly low or zero levels, a scan is carried out prior to surgery to show the localization of the tumor. During the surgical procedure to remove the tumor, a probe capable of detecting radioactivity is used to determine whether the surgeon has removed the entire tumor or whether the surgery should be extended until the entire tumor has been removed. Samples of tissues obtained during the surgery can be examined histologically and by methods which detect radioactivity will enhance the information obtained by the probe and will further assist the surgeon in arriving at a decision as to whether the removal of the tumor has been complete.

The present invention provides a mode of therapy in which the cytotoxic effect and cancer cell killing process is achieved by the administration of a binary reagent having two moieties, the first moiety being a targeting agent with a substantial affinity for the antigenic receptors capable of endocytosis on target cells, the target cells being cancer cells, the second moiety of the binary reagent being a soluble precipitable material which has been heavily radio-labeled. Permitting the binary reagent to be endocytosed by the target cancer cells, the endocytosing and lysosome enzymes causing the detachment of the soluble precipitable material from the targeting agent moiety of the binary reagent and converting the soluble precipitable material into an insoluble molecule which precipitates and accumulates as a radioactive toxic precipitate in the target cancer cells.

Continuing the administration of the binary reagent to accumulate a sufficient amount of the radioactive toxic precipitate and having the radioactive toxic precipitate remain inside the targeted cells for an extended period of time will generate micro-regions of supra-lethal radiation called Hot-Spots. All cells within each Hot-Spot are killed, non-selectively by the intense radiation field, irrespective of whether the cells are targeted or not, whether the cells accumulated precipitate or nor, whether the cells are sensitive or resistant, or whether the cells are malignant or nonmalignant. Furthermore, the intense radiation field overwhelms the adaptive mechanisms of the cancer cells and prevents tumor cells from adapting, surviving, becoming resistant, and seeding to create a tumor population of resistant cells.

The present invention can also be used to detect physiological and pathological changes in normal tissues. For example, normal liver parenchymal cells have 100,000 to 150,000 receptors which specifically bind clusters of galactose residues which are present on a number of natural and synthetic ligands having galactose residues, including desylated fetuin, lactosylated polylysine, lactosylated albumin, and galactose molecules attached to polymers. The lactosylated polylysine can act as the liver specific targeting moiety of a binary reagent, the other moiety being a trace labeled soluble precipitable material. Upon binding the ligand moiety of the binary reagent, the liver receptors endocytose and recycle back to the cell surface about 10 times per hour. The targeting moiety of the binary reagent is digested in the lysosomes and the soluble precipitable material moiety of the binary reagent is converted by the lysosomal enzymes in the liver cells to an insoluble material which precipitates and accumulates in the liver cells. Liver cells that have been injured have less receptors on each cell and this reduction can be detected by a scan by a reduction in the amount of precipitate which accumulates in the liver cells after a standard amount of binary reagent has been administered. Malignant tumors of the liver, compared to normal liver cells, have a much lower number of the galactose specific receptors, there being a zero to 10,000 receptors per liver cancer cell. The administration of a binary reagent composed of a ligand specific for the liver receptors attached to a trace labeled soluble precipitable material will accumulate significantly less in the tumor compared to the normal liver and the scan will detect the presence of the tumor by the tumor being less radioactive than the normal liver.

The method of the present invention has wide application as a research tool for determining the ligand-receptor relationship of specific proteins. Current methods for studying ligand-receptor relationship are carried out in tissue culture and in vivo and use a labeled ligand, such as an antibody, to bind to the cells which are examined to measure receptor binding parameters and endocytic function. As described, tissue culture methods have inherent problems which are unlikely to be solved because the conditions in culture cannot replicate the complex in vivo environment which influence receptor number amongst many other cell characteristics. In addition to the problems which are inherent and particular to tissue culture, current methods which use ligand binding to receptors and endocytosis of binary reagents and detachment of a soluble material in the lysosomes of the targeted cells suffer from disadvantages which are operative both in tissue culture and in vivo. The number of ligands that bind to each cell is limited by the number of receptors, this number being fixed and, as is the case for many ligands, being so small that the binding of the ligand, labeled with various tracer materials such as fluorescent molecules and radioisotopes, cannot be detected. Because of this problem, it is likely that many proteins which are actually ligands for a particular cell type have not been identified as ligands. A similar problem also exists in detecting ligands which induce endocytosis because the soluble trace labeled molecule attached to the ligand which is detached in the lysosomes does not remain trapped in the lysosomes. As a consequence, the number of the tracer chemical which is present in the lysosomes at any one time is relatively low and becomes lower with the lapse of time after the administration of the binary reagent has been completed, and while waiting for the binary reagent in the extracellular fluid surrounding the cells to be eliminated, an elimination which is necessary to reduce the background "noise" of trace labeled chemical in the extracellular fluid. In vivo attempts to reduce this problem have used the administration of a large dose of the binary reagent which introduce a further problem. Specificity of natural circulating ligands in the living host is achieved, in part, by the concentration of the ligand being so low that the ligand binds virtually exclusively to cells having a large number of ligand-specific receptors and/or having receptors which bind the ligand with a high affinity. A high non-physiological concentration of ligand thus reduces the specificity of the ligand because many cells having a low number of receptors and/or receptors with a low binding affinity will also bind the ligand. The method of the present invention overcomes these difficulties because the trace labeled soluble precipitable material upon being detached from the targeting moiety of the binary reagent is converted by the intracellular enzymes into an insoluble material which precipitates and accumulates in the targeted cells. The amount of precipitate which accumulates in the cells continues to increase as long as the administration of the binary reagent continues. In 100 hours the number of molecules which accumulate as a precipitate can be 1,000 times greater than the number of receptors on the cell. Moreover, the accumulated precipitate remains in the cell for an extended period of time so the cells and tissues can be examined at a time when there is a zero background of the tracer labeled material in the extracellular fluid and they can be examined by methods which are likely to allow soluble chemicals from escaping from the cells during the preparation of the cells for examination. The present invention enables the candidate ligand attached to the soluble precipitable material to be administered to the living host at a very low dose to achieve blood concentrations of the ligand at the low levels that occur naturally in the living host and which contribute to the specificity achieved in the host. After the Accurate determination of ligand-receptor relationships has great value in determining the function of proteins coded by isolated genes, as in the human genome project, and determining the specificity of ligands to be used as the targeting agent for normal and cancer cells, the targeting agent being used to make the most effective binary reagents for the purpose of therapy and diagnostic scanning.

The method of the present invention also permits the permanently "labeled" cell to be easily identified and followed, even if the should divide, change its function, receptor status or anatomical location. The potential to label and follow cells in such a simple and cost effective manner has value in many biological studies such as in developmental biology and in cancer.

What is claimed is:

1. A method for accumulating a trace-labeled or therapeutic precipitate in targeted cells of a living host for the conducting of procedures dependent upon the accumulation of the precipitate including diagnosis, therapy, biological testing of ligand receptor relationships, and monitoring, the living host being composed of at least a first population of first target cells having a first antigenic receptor which is capable of binding a first targeting agent and which is capable of endocytosis when the first targeting agent binds to the first antigenic receptor, and a second population of non-target cells;

the method comprising the steps of:

introducing into the living host a soluble binary reagent selected from the group consisting of the first targeting agent which has substantial affinity for the first antigenic receptors and a trace-labeled or therapeutic soluble precipitable material which is attached to the first targeting agent;

permitting the soluble binary reagent to be endocytosed into the lysosomes of the first target cells, the endocytosing and the natural intra-cellular enzymes in the lysosomes of the cells causing the trace-labeled or therapeutic soluble precipitable material to detach from the first targeting agent and thereby enabling the detached soluble precipitable material to form a trace-labeled or therapeutic precipitate accumulating in the first target cells, each molecule of precipitate being formed from a molecule of the soluble precipitable material and being selected from the group consisting of a first antigenic epitope being an epitope which is an integral part of the structure of the precipitate, a second antigenic epitope, and a neo-antigenic third epitope; and continuing the introducing of the soluble binary reagent into the living host to thereby increase the amount of the accumulation of the trace-labeled or therapeutic precipitate in the first target cells to form a plurality of antigenic epitopes the number of which is proportional to the amount of molecules of accumulation of the precipitate in the first target cells.

2. A method in accordance with claim 1 in which the trace-labeled or therapeutic soluble precipitable material is an organic chemical selected from the group consisting of peptides including opio-melanins, carbohydrates including cellulose, chitosan, and chitin, of synthetic polymers, and of indoxyl compounds having molecular positions 1–7.

3. A method in accordance with claim 2 in which the indoxyl compounds are selected from the group consisting of sulphates, phosphates glycosides, and the like which when attached to position 3 of the indoxyl compounds are cleavable by the natural intra-cellular enzymes in the lysosomes, the material remaining after cleaving at position 3 being a soluble reactive intermediate molecule which is rapidly oxidized in the natural environment of the host cell, the oxidized soluble intermediate spontaneously dimerizing and thereby forming the trace-labeled or therapeutic precipitate which has a neoantigenic third epitope not present on the indoxyl compounds from which the precipitate was formed.

4. A method in accordance with claim 2 in which each of the indoxyl compounds includes a substance which when attached to at least one of positions 4, 5, 6, and 7 of the indoxyl compound alters the characteristics of the indoxyl compounds and the precipitate thereof.

5. A method in accordance with claim 2 in which each of the indoxyl compounds includes phenyl compounds attached at position 5 of the indoxyl compound to alter the characteristics of the indoxyl compounds and the precipitate thereof.

6. A method in accordance with claim 2 in which each of the indoxyl compounds includes benzyloxy compounds and derivatives of benzyloxy compounds attached at position 5 of the indoxyl compounds to alter the characteristics of the indoxyl compounds and the precipitate thereof.

7. A method in accordance with claim 2 in which each of the indoxyl compounds includes 5,5-bi-indoxyls attached at position 5 of the indoxyl compounds to alter the characteristics of the indoxyl compounds and the precipitate thereof.

8. A method in accordance with claim 2 in which the indoxyl compounds have a first chemical attached to positions 4, 5, 6, and 7 of the indoxyl compounds to reduce substantially the rate of exit from the cells of the soluble indoxyl compound prior to the soluble indoxyl compounds forming the precipitate.

9. A method in accordance with claim 8 in which the first chemical is attached to the indoxyl compounds by a bond which is incapable of being cleaved by mammalian and non-mammalian enzymes.

10. A method in accordance with claim 2 in which a second chemical is attached to the indoxyl compounds at positions 4, 5, 6, or 7, the second chemical having an antigenic epitope which is present as the second antigenic epitope on the precipitate.

11. A method according to claim 1 in which the soluble precipitable material is radio-labeled.

12. A method in accordance with claim 1 in which the soluble precipitable material is converted by the natural intra-cellular enzymes into an intra-cellular precipitate, the intra-cellular precipitate later becoming the first extra-cellular precipitate.

13. A method in accordance with claim 1 in which the soluble precipitable material is inherently soluble material which when detached from the first targeting agent is converted by at least one of the natural intra-cellular enzymes into the precipitate.

14. A method in accordance with claim 1 in which the soluble precipitable material which is converted by at least one of the natural intra-cellular enzymes into the precipitate has a neo-antigenic third epitope.

15. A method in accordance with claim 1 in which the soluble precipitable material is converted by at least one of the natural intra-cellular enzymes in the lysosomes into a soluble intermediate molecule, the soluble intermediate molecule being converted by the natural environment in the host cells into the precipitate.

16. A method in accordance with claim 1 in which the soluble intermediate molecule is rapidly oxidized by the natural environment in the host cell, the oxidized soluble intermediate molecule spontaneously dimerizing and thereby making an insoluble molecule which forms the precipitate which has a neo-antigenic third epitope not present on the soluble precipitable material from which the precipitate was formed.

17. A method in accordance with claim 1 in which the soluble precipitable material includes both a third and a fourth soluble chemicals, each of the third and fourth soluble chemicals being attached to the targeting agent, the third and fourth soluble chemicals when detached from the targeting agent, reacting with each other to form the precipitate.

18. A method in accordance with claim 1 in which the trace-labeled or therapeutic soluble precipitable material is selected from the group consisting of a chemical including diatonic amphiphilic compounds including tilorone and acradine orange, the soluble precipitable material upon being detached from the targeting agent reacting with the product formed endogenously by the cancer cells and the normal cells, the product precipitating inside the targeted cells and the trace-labeled or therapeutic precipitate so formed becoming relatively non-digestible.

19. A method in accordance with claim 1 in which the soluble precipitable material is composed of a soluble moiety and insoluble moiety, the soluble precipitable material being converted by the natural intra-cellular enzymes into the precipitate.

20. A method in accordance with claim 1 in which the soluble precipitable material is composed of a soluble moiety and insoluble moiety, the soluble precipitable material being converted by the natural intra-cellular enzymes into the precipitate which has a neo-antigenic third epitope.

21. A method in accordance with claim 1 in which the trace-labeled or therapeutic soluble precipitable material to be endocytosed into the lysosomes of the first target cells has a soluble moiety and an insoluble moiety, the soluble moiety having a solubilizing effect on the insoluble moiety and being cleaved by the natural intra-cellular enzymes in the lysosomes from the insoluble moiety, the solubilizing effect of the soluble moiety on the insoluble moiety being thereby dissipated and enabling the remaining material, being insoluble, spontaneously to form the trace-labeled or therapeutic precipitate.

22. A method in accordance with claim 1 in which the trace-labeled or therapeutic soluble precipitable material to be endocytosed into the lysosomes of the first target cells has a soluble moiety and an insoluble moiety, the soluble moiety having a solubilizing effect on the insoluble moiety, the soluble moiety being at least partially digested by the natural intra-cellular enzymes in the lysosomes and thereby dissipating the solubilizing effect of the soluble moiety on the insoluble moiety, the insoluble moiety in response spontaneously forming the trace-labeled or therapeutic precipitate.

23. A method in accordance with claim 1 in which the trace-labeled or therapeutic soluble precipitable material to be endocytosed into the lysosomes of the first target cells has a soluble moiety and an insoluble moiety, the soluble moiety having a peptide moiety with a substantial binding affinity for the insoluble moiety, the peptide moiety of the soluble moiety being partially digested by the natural intra-cellular enzymes in the lysosomes, the binding affinity of the peptide moiety being dissipated by the partially digesting by the material intra-cellular enzymes and thereby detaching the soluble moiety and eliminating the solubilizing effect of the soluble moiety, the remaining insoluble moiety of the soluble precipitable material spontaneously forming the trace-labeled or therapeutic precipitate.

24. A method in accordance with claim 1 in which the trace-labeled or therapeutic soluble precipitable material has a first chemical attached thereto to reduce substantially the rate of exit from the molecules of the soluble precipitable material prior to the soluble precipitable material forming the trace-labeled or therapeutic precipitate.

25. A method in accordance with claim 1 in which the first antigenic epitope is a portion of the precipitate and is a portion of the soluble precipitable material from which the precipitate was formed.

26. A method in accordance with claim 1 in which a second chemical is attached to the soluble precipitable material, the second chemical having an antigenic epitope which is present as the second antigenic epitope on the precipitate.

27. A method in accordance with claim 1 in which the second antigenic epitope on the precipitate is capable of being cleaved by non-mammalian enzymes and incapable of being cleaved by mammalian enzymes.

28. A method in accordance with claim 1 in which the trace-labeled or therapeutic precipitate is selected from a group consisting of a non-metabolizable material and a material slowly metabolizable by at least one of mammalian enzymes and non-mammalian enzymes.

29. A method in accordance with claim 28 in which the precipitate is slowly metabolizable at a rate which can be controlled by the properties of the materials forming the precipitate.

30. A method in accordance with claim 1 in which the trace-labeled or therapeutic precipitate is selected from a group consisting of a random structure and an ordered structure such as one of a linear polymer.

31. A method in accordance with claim 1 in which the trace-labeled or therapeutic precipitate is selected from a group consisting of insoluble and slightly soluble in the extra-cellular fluid found in the living host.

32. A method in accordance with claim 1 and further comprising the step of further administering a non-mammalian free enzyme to the living host, the non-mammalian free enzyme being adapted to alter the precipitate formed in the extra-cellular fluid and resulting in antibodies and peptides which have an affinity for the precipitate to be unable to bind to the precipitate.

33. The method in accordance to claim 32 in which the altering of the precipitate comprising the cleaving of the second antigenic epitope of the precipitate.

34. A method in accordance with claim 32 in which the altering of the precipitate comprising the digesting of the precipitate.

35. A method in accordance with claim 32 and further comprising the step of still further administering to the living host an agent which greatly increases the rate of elimination of the free non-mammalian enzyme from the extra-cellular fluid.

36. A method in accordance with claim 32 and further comprising the step of still further administering to the living host an agent which inhibits the action of the free non-mammalian enzyme.

* * * * *